US00PP27347P3

(12) United States Plant Patent
Danziger

(10) Patent No.: US PP27,347 P3
(45) Date of Patent: Nov. 1, 2016

(54) ***ANGELONIA* PLANT NAMED 'DALONVIOLT'**

(50) Latin Name: *Angelonia angustifloria*
Varietal Denomination: DALONVIOLT

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farms (IL)

( * ) Notice: Subject to any disclaimer, the term of this patent is extended or adjusted under 35 U.S.C. 154(b) by 36 days.

(21) Appl. No.: 14/544,751

(22) Filed: Feb. 12, 2015

(65) Prior Publication Data

US 2016/0242348 P1 Aug. 18, 2016

(51) Int. Cl.
*A01H 5/02* (2006.01)

(52) U.S. Cl.
USPC ..... Plt./404

(58) Field of Classification Search
USPC ..... Plt./404
See application file for complete search history.

*Primary Examiner* — Annette Para
(74) *Attorney, Agent, or Firm* — Cassandra Bright

(57) ABSTRACT

A new and distinct *Angelonia* cultivar named 'DALONVIOLT' is disclosed, characterized by a compact and free branching plant habit, freely flowering and good garden performance. Flowers are colored violet and white. The new variety is a *Angelonia*, normally produced as an outdoor garden or container plant.

2 Drawing Sheets

Latin name of the genus and species: *Angelonia angustifloria.*

Variety denomination: 'DALONVIOLT'.

BACKGROUND OF THE INVENTION

The new *Angelonia* cultivar is the product of a planned breeding program conducted by the inventor, Gavriel Danziger, in Moshav Mishmar Hashiva, Israel. The objective of the breeding program was to produce new *Angelonia* varieties for ornamental commercial ornamental applications. The cross resulting in this new variety was made during April of 2011.

The seed parent is the unpatented, proprietary variety referred to as *Angelonia* 'AL 679'. The pollen parent is the unpatented, propriety variety referred to as *Angelonia* 'AL 687'. The new variety was discovered in June of 2012 by the inventor in a group of seedlings resulting from the 2011 crossing, in a research greenhouse in Moshav Mishmar Hashiva, Israel.

Asexual reproduction of the new cultivar was performed by vegetative terminal cuttings. This was first performed at a research greenhouse in Moshav Mishmar Hashiva, Israel in July of 2012 and has shown that the unique features of this cultivar are stable and reproduced true to type in multiple successive generations.

SUMMARY OF THE INVENTION

The cultivar 'DALONVIOLT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DALONVIOLT' These characteristics in combination distinguish 'DALONVIOLT' as a new and distinct *Angelonia* cultivar:

1. Compact growth habit.
2. Free branching habit
3. Free flowering habit.
4. Good garden performance.
5. Violet and white flower coloration Plants of the new cultivar 'DALONVIOLT' are similar to plants of the seed parent, *Angelonia* 'AL 679' in most horticultural characteristics, however, plants of the new cultivar 'DALONVIOLT' differ in the following;

1. Flower color of the parent is lighter.
2. Flower size of the parent is larger.

Plants of the new cultivar 'DALONVIOLT' are similar to plants of the pollen parent, *Angelonia* 'AL 687' in most horticultural characteristics, however, plants of the new cultivar 'DALONVIOLT' differ in the following;

1. Flower color of the parent is white and that of the new variety is violet and white.
2. Growth habit of the parent is vigorous and rangy; that of the new variety is compact.
3. Flower size of the parent is larger.

COMMERCIAL COMPARISON

Plants of the new cultivar 'DALONVIOLT' are comparable to the commercial variety *Angelonia* 'DALON11'. U.S. application Ser. No. 13/986,279. The two *Angelonia* varieties are similar in most horticultural characteristics; however, the new variety 'DALONVIOLT' differs in the following:

1. Lighter flower color than comparator.
2. More compact than comparator.
3. More branches per plant than comparator.

Plants of the new cultivar 'DALONVIOLT' can also be comparable to the patented commercial variety *Angelonia* 'DALON9' U.S. Plant Pat. No. 22,912. The two *Angelonia* varieties are similar in most horticultural characteristics; however, the new variety 'DALONVIOLT' differs in the following:

1. Lighter flower color than comparator.
2. More compact than comparator.
3. More branches per plant than comparator.

BRIEF DESCRIPTION OF THE PHOTOGRAPHS

The accompanying photograph in

Figure 1:
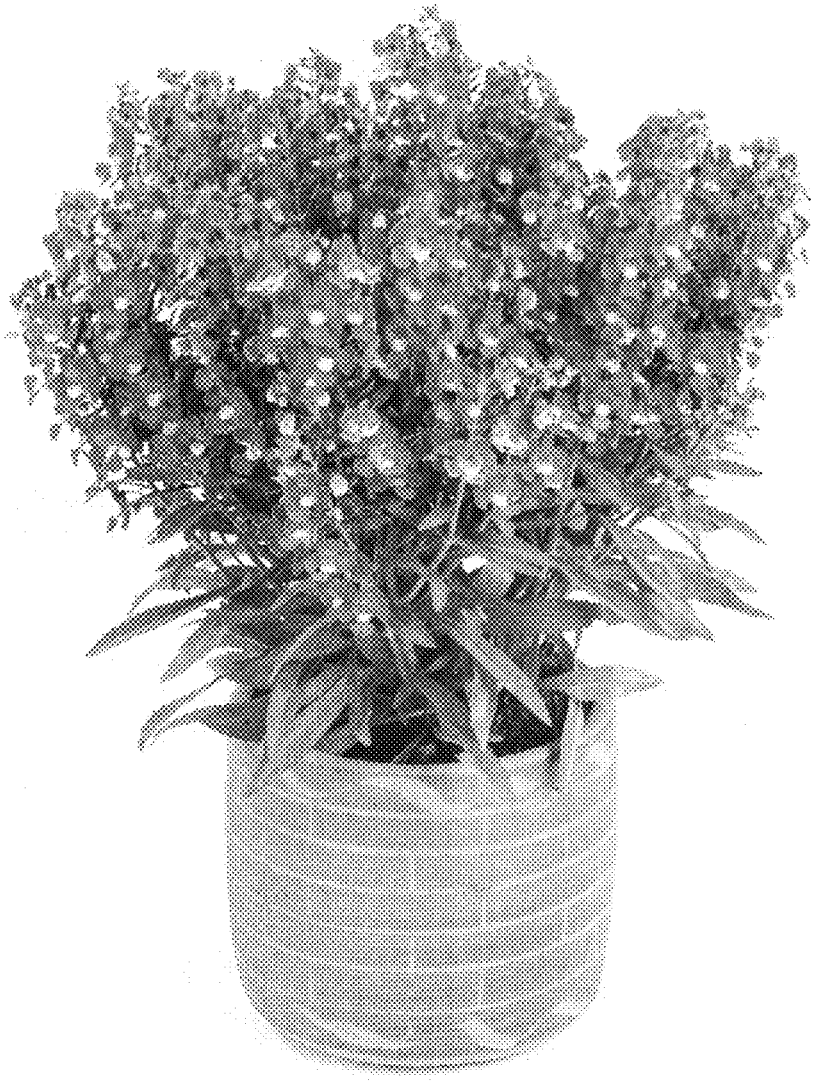
FIG. 1 illustrates in full color a typical plant of 'DALONVIOLT' grown outdoors, in a 13 cm pot. Age of the plant photographed is approximately 60 days from a rooted cutting.
Figure 2:
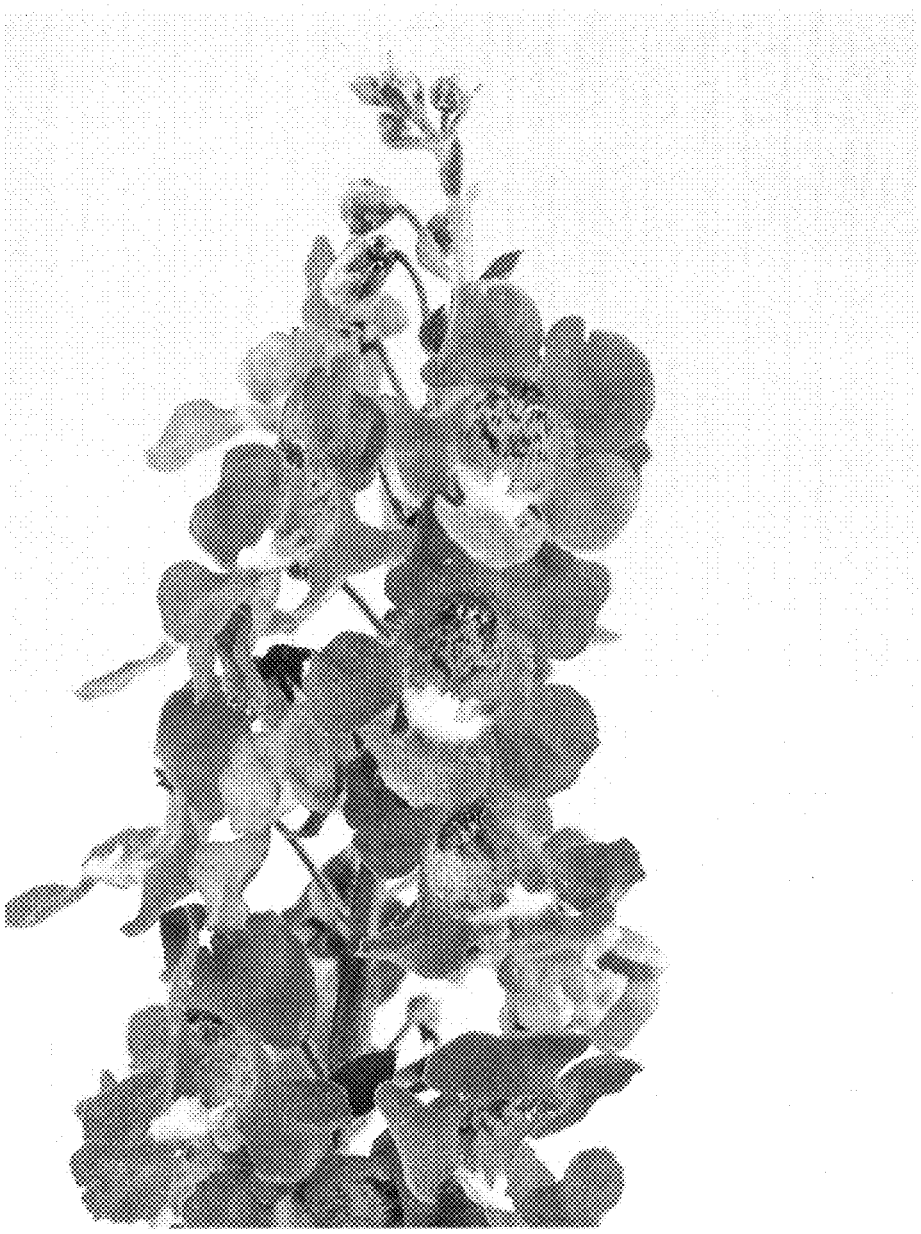
FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DALONVIOLT' plants grown in a greenhouse, in Moshav Mishmar Hashiva, Israel. The growing temperature ranged from 20° C. to 30° C. during the day and from 15° C. to 25° C. during the night. General light conditions are bright, normal sunlight. Measurements and numerical values represent averages of typical plant types. Botanical classification: *Angelonia* 'DALONVIOLT'.

PROPAGATION

Type of propagation typically used: Cutting.
Time to initiate roots: 10-15 days.
Root description: Fibrous and well branched.

PLANT

Age of plant described: Approximately 70 days.
Container size of the plant described: 13 cm.
Growth habit: Erect.
Height:
- *To top of foliage.*—20 cm.
- *To top of flowers.*—25 cm.

Plant spread: 26 cm.
Growth rate: Fast.
Branching characteristics: Strong.
Length of primary lateral branches: 25 cm.
Diameter of lateral branches: 0.5 cm.
Quantity of primary lateral branches: 10-12.
Characteristics of primary lateral branches:
- *Form.*—Round.
- *Diameter.*—0.5 cm.
- *Color.*—Near RHS Yellow-green 144C.
- *Texture.*—Puberulous.
- *Strength.*—Somewhat rigid.

Internode length: 2-2.5 cm.

FOLIAGE

Leaf:
- *Arrangement.*—Opposite.
- *Quantity.*—Approximately 25-30 per branch.
- *Average length.*—1.5-3.5 cm.
- *Average width.*—0.5-1.0 cm.
- *Shape of blade.*—Lance.
- *Apex.*—Sharply pointed.
- *Base.*—Wedge Shaped.
- *Margin.*—Scalloped.
- *Texture of top surface.*—Smooth.
- *Texture of bottom surface.*—Smooth.
- *Pubescence.*—No.
- *Aspect.*—50°.
- *Color.*—Young foliage upper side: Near RHS Green 143A. Young foliage under side: Near RHS Green 143C. Mature foliage upper side: Near RHS Yellow-green 147A. Mature foliage under side: Near RHS Yellow-green 147B.
- *Venation.*—Type: Pinnate. Venation color upper side: Near RHS Yellow-green 147C. Venation color under side: Near RHS Yellow-green 147C.
- *Petiole.*—None.

FLOWER

Natural flowering season: Spring, Summer and Autumn.
Days to flowering from rooted cutting: 60.
Inflorescence and flower type and habit: Panicle.
Rate of flower opening: 7 to 14 days from bud to fully opened flower.
Flower longevity on plant: 5-8 days.
Persistent or self-cleaning: Self Cleaning.
Bud:
- *Shape.*—Round.
- *Length.*—0.5 cm.
- *Diameter.*—0.5 cm.
- *Color.*—Near RHS Yellow-green 150C.

Flower size:
- *Diameter.*—3 cm.
- *Length.*—2.5 cm.

Petals:
- *Length.*—1 cm.
- *Diameter.*—1.2 cm.
- *Quantity.*—5.
- *Texture.*—Smooth.
- *Apex.*—Rounded.
- *Color.*—When opening: Upper surface: Near RHS Violet 83C, base near White NN155C. Lower surface: Near RHS Violet 83D base near Green-Yellow 2D. Fully opened: Upper surface: Near RHS Violet 83D base near White NN155C. Lower surface: Near RHS Violet 83D base near White NN155C.

Sepals:
- *Quantity per flower.*—5.
- *Shape.*—Ovate.
- *Length.*—0.2 cm.
- *Width.*—0.1 cm.
- *Apex.*—Acute.
- *Base.*—Attenuate.
- *Margin.*—Entire.
- *Texture.*—Puberulous, all surfaces.
- *Color.*—Near RHS Yellow-green 146A.

Pedicel:

*Length.*—1.5-2 cm.

*Diameter.*—0.1 cm.

*Color.*—Near RHS Green N137A.

Fragrance: Faint, delicate sweet scent.

REPRODUCTIVE ORGANS

Stamens:

*Number.*—4.

*Filament length.*—3 mm.

Anthers:

*Shape.*—Eliptic.

*Length.*—2 mm.

*Color.*—Near RHS Violet 86A.

Pollen:

*Color.*—Near RHS White 155D.

*Quantity.*—Moderate.

Pistil:

*Number.*—1.

*Length.*—0.3 cm.

*Style.*—Length: 0.4 cm. Color: Near RHS White NN155D.

*Stigma.*—Shape: Thorn. Color: Near RHS White 155A.

OTHER CHARACTERISTICS

Seeds and fruits: If present, round capsule about 0.3-0.5 cm long with 50-75 seeds.

Disease/pest resistance: Neither resistance nor susceptibility to the normal diseases and pests of *Angelonia* have been observed. Pests common to *Angelonia* include Aphids and thrips. Typical diseases are *Botrytis* and *Pythium.*

Temperature tolerance: 10°-35°.

What is claimed is:

1. A new and distinct cultivar of *Angelonia* plant named 'DALONVIOLT' as herein illustrated and described.

* * * * *